(12) United States Patent
Brady et al.

(10) Patent No.: US 11,900,518 B2
(45) Date of Patent: Feb. 13, 2024

(54) INTERACTIVE SYSTEMS AND METHODS

(71) Applicant: VirtTuri Limited, Stowmarket (GB)

(72) Inventors: Peter Alistair Brady, Stowmarket (GB); Hayden Allen-Vercoe, Hemyock (GB); Sathish Sankarpandi, Ipswich (GB); Ethan Dickson, Ipswich (GB)

(73) Assignee: VirtTari Limited, Stowmarket (GB)

( * ) Notice: Subject to any disclaimer, the term of this patent is extended or adjusted under 35 U.S.C. 154(b) by 309 days.

(21) Appl. No.: 17/441,791

(22) PCT Filed: Sep. 17, 2019

(86) PCT No.: PCT/GB2019/052611
§ 371 (c)(1),
(2) Date: Sep. 22, 2021

(87) PCT Pub. No.: WO2020/193929
PCT Pub. Date: Oct. 1, 2020

(65) Prior Publication Data
US 2022/0172710 A1 Jun. 2, 2022

(30) Foreign Application Priority Data
Mar. 22, 2019 (GB) .................................. 1903984

(51) Int. Cl.
*G06T 13/20* (2011.01)
*G06V 40/16* (2022.01)
(Continued)

(52) U.S. Cl.
CPC ........... *G06T 13/205* (2013.01); *G06N 3/044* (2023.01); *G06V 10/7553* (2022.01);
(Continued)

(58) Field of Classification Search
USPC ...................................................... 704/1–504
See application file for complete search history.

(56) References Cited

U.S. PATENT DOCUMENTS 10,799,186 B2 * 10/2020 Howard ............... A61B 5/7282
2011/0115798 A1 * 5/2011 Nayar ..................... G06T 13/40
345/473

(Continued)

FOREIGN PATENT DOCUMENTS

WO  WO 2020/193929  10/2020

OTHER PUBLICATIONS

International Preliminary Report on Patentability dated Jun. 10, 2021 From the International Preliminary Examining Authority Re. Application No. PCT/GB2019/052611. (35 Pages).

(Continued)

*Primary Examiner* — Marcus T Riley

(57) ABSTRACT

A method of producing an avatar video, the method comprising the steps of:
providing a reference image of a person's face; providing a plurality of characteristic features representative of a facial model X0 of the person's face, the characteristic features defining a facial pose dependent on the person speaking; providing a target phrase to be rendered over a predetermined time period during the avatar video and providing a plurality of time intervals t within the predetermined time period; generating, for each of said times intervals t, speech features from the target phrase, to provide a sequence of speech features; and generating, using the plurality of characteristic features and sequence of speech features, a sequence of facial models Xt for each of said time intervals t.

20 Claims, 16 Drawing Sheets

(51) Int. Cl.
*G06V 10/82* (2022.01)
*G06V 10/75* (2022.01)
*G10L 15/16* (2006.01)
*G10L 15/25* (2013.01)
*G10L 21/10* (2013.01)
*G06N 3/044* (2023.01)
*G06V 10/764* (2022.01)
*G10L 15/08* (2006.01)

(52) U.S. Cl.
CPC ............ *G06V 10/764* (2022.01); *G06V 10/82* (2022.01); *G06V 40/168* (2022.01); *G10L 15/16* (2013.01); *G10L 15/25* (2013.01); *G10L 21/10* (2013.01); *G10L 2015/088* (2013.01); *G10L 2021/105* (2013.01)

(56) References Cited

U.S. PATENT DOCUMENTS

2012/0130717 A1* 5/2012 Xu .................... G06T 13/40
345/473
2012/0280974 A1* 11/2012 Wang .................... G10L 21/10
345/419
2019/0130628 A1* 5/2019 Cao .................... G10L 21/10
2022/0172710 A1* 6/2022 Brady .................... G06N 3/044

OTHER PUBLICATIONS

International Search Report and the Written Opinion dated Sep. 17, 2020 From the International Searching Authority Re. Application No. PCT/GB2019/052611. (24 Pages).

Bitouk et al. "Creating A Speech Enabled Avatar From A Single Photograph", 2008 IEEE Virtual Reality Conference, XP031340006, Reno, Nevada, USA, Mar. 8-12, 2008, p. 107-110, Mar. 8, 2008.

Chen et al. "A Realistic Face-to-Face Conversation System Based on Deep Neural Networks", ArXiv Preprint ArXiv:1908.07750v1, XP081466712, p. 1-10, Aug. 21, 2019.

Fan et al. "A Deep Bidirectional LSTM Approach for Video-Realistic Talking Head", Multimedia Tools and Applications, XP035924707, 75(9): 5287-5309, Sep. 29, 2015.

Kuhnke et al. "Visual Speech Synthesis From 3D Mesh Sequences Driven by Combined Speech Features", 2017 IEEE International Conference on Multimedia and EXPO, ICME 2017, Hong Kong, China, Jul. 10-14, 2017, XP033146759, p. 1075-1080, Jul. 10, 2017.

* cited by examiner

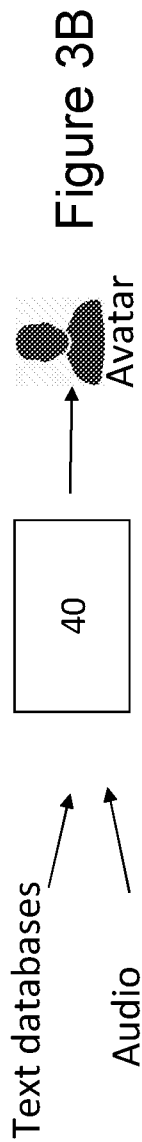
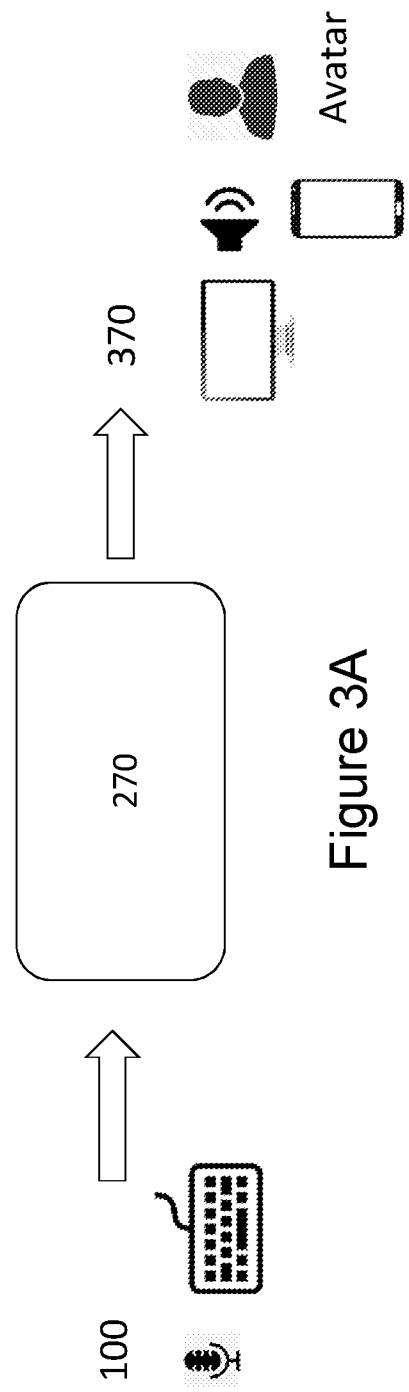
Figure 3B
Figure 3A

INTERACTIVE SYSTEMS AND METHODS

RELATED APPLICATIONS

This application is a National Phase of PCT Patent Application No. PCT/GB2019/052611 having International filing date of Sep. 17, 2019, which claims the benefit of priority of United Kingdom Patent Application No. 1903984.1 filed on Mar. 22, 2019. The contents of the above applications are all incorporated by reference as if fully set forth herein in their entirety.

Field and Background of the Invention

The present disclosure relates generally to interactive health care systems and methods.

In particular, the disclosure relates to providing a speech-driven, audio-visual avatar (anthropomorphous model) of a doctor or a nurse, which may be employed in a virtual environment or advanced man-machine interfaces such as specialised digital assistants. The avatar is not only very realistic but can accurately answer health-care related questions, being provided within a platform of machine learning and deep learning based applications to accurately answer questions posed in the natural language by users.

Health care providers offer health care services to patients on a daily basis. In the United Kingdom, general practitioner doctors, referred to as GPs, are experiencing increased pressure partly due to insufficient government funding available for the National Health Service (NHS). A further factor in the increased workload of health care providers is an increasingly ageing population with older patients being more likely to develop health conditions and require more visits to the GPs.

Particularly, addressing self-treatable minor ailments such as colds, coughs, flu, bad back and hay fever costs the NHS around £2bn* per annum (*PAGB). GPs are currently under immense pressure, with significant amounts of money devoted to dealing with minor ailments (51.4 m minor ailment consultations every year). This comes at a time when the NHS is required to find £22 billion of efficiency savings by 2020 (*PAGB).

As it becomes harder to secure a GP appointment and more convenient to search for information online, the core population is showing a dangerous over-reliance upon the so-called 'Dr Google' to self-diagnose their symptoms. In fact, 1 in 20 Google searches is now health related. Currently, it is estimated that one in four internet users self-diagnose on the internet instead of visiting their GP. This proliferation of internet use for health information offers a mixed bag of valuable and misleading or junk information. It has been reported that 25% of women misdiagnose themselves on the internet (Daily Mail, 2012). Misdiagnosis leads to mistreatment, potentially endangering life through misinformation, which effectively puts further strain on the NHS.

In recent years, a number of online applications or digital assistants have been developed to address these concerns. The applications aim to answer questions asked by a user and provide answers or advice. Users, however, often find such applications too generic and non-engaging ('robotic'). Furthermore, such automated systems suffer from major reliability issues (one example is Facebook™ chatbots hitting a 70% failure rate).

Aspects of the present invention aim to address the above-mentioned problems.

SUMMARY OF THE INVENTION

Solutions to the problems set out above are provided in the claimed aspects of the invention. These relate to avatar video technology and ground-breaking artificial intelligence (AI) and avatar video technology. Taken either individually or, preferably, in combination, these solutions can serve medically approved information from a video realistic avatar, accessible 24/7, which is both reliable and engaging to the user.

In a first independent aspect of the present invention there is provided a method of producing an avatar video, the method comprising the steps of:
 providing a reference image of a person's face;
 providing a plurality of characteristic features representative of a facial model $X_0$ of the person's face, the characteristic features defining a facial pose dependent on the person speaking;
 providing a target phrase to be rendered over a predetermined time period during the avatar video and providing a plurality of time intervals t within the predetermined time period;
 generating, for each of said times intervals t, speech features from the target phrase, to provide a sequence of speech features; and
 generating, using the plurality of characteristic features and sequence of speech features, a sequence of facial models $X_t$ for each of said time intervals t.

Advantageously, the sequence of facial models is generated using characteristic features defining a facial pose as well as speech features. This results into a speech-driven sequence of facial models and thus a highly realistic avatar video.

Preferably, the characteristic features defining a facial pose comprise landmark points (landmarks) known from Active Shape Models (ASMs), as well as latent descriptors (vectors) representing abstract appearance features such as colour, texture etc. The characteristic features define a facial pose dependent on the person speaking. A pose preferably includes both high-level positional information i.e. gaze direction, head alignment, as well as capturing specific facial features and expressions.

Preferably, the plurality of characteristic features comprises at least one Active Shape Model (ASM) landmark, and at least one latent descriptors representing abstract appearance features. The at least one latent descriptor may be extracted using a Deep Convolutional Network (DCN).

Speech features are defined as abstract quantifiers of audio information such as, but not limited to, short-time-frequency representations i.e. mel-frequency cepstral coefficients (MFCCs), per-frame local energy, delta coefficients, zero-cross rate etc. Preferably, the speech features are extracted with a phonetic classifier module using a Deep Convolutional Network (DCN).

Preferably, the method further comprises the step of generating, from the sequence of facial models $X_t$, a sequence of face images to produce the avatar video.

The target phrase may be provided as text data. Alternatively, or in addition to the text data, the target phrase may contain audio data.

Preferably, at least one of said speech features comprises a phonetic label. Phonetic labels are preferably generated at pre-set time intervals to provide a phonetic label for each video frame.

Preferably, the sequence of facial models Xt is generated using a recursive model. The recursive model is preferably based on Long Short-Term Memory networks (LSTMs) comprising internal contextual state cells, wherein the output of the LSTM network is modulated by the state of the contextual state cells. This is an advantageous property when the prediction of the neural network is to depend on the historical context of inputs, rather than only on the very last input.

Generating the sequence of face images comprises may use a frame generator to combine the reference image with the sequence of facial models Xt.

Preferably, the frame generator comprises a discriminator module using at least one loss function for reducing differences between the reference image and each of the facial models Xt in said sequence of facial models Xt.

In a second independent aspect of the present invention, there is provided a method for providing an answer to a user, the method comprising the steps of:
  providing a database comprising an indexed question library and a plurality of responses;
  providing a correlation between the indexed question library and the plurality of responses;
  receiving a question from the user as user input;
  searching keyword information in the indexed question library based on the user input; and
  providing at least one response to the user based on said correlation.

The method may be implemented in an information retrieval system. Preferably, the method further comprises the step of:
  receiving feedback input from the user in response to the at least one response provided to the user; and based on the feedback input, searching further keyword information in the indexed symptoms library; and providing at least one further response to the user based on said correlation.

Advantageously, the answer retrieval process is guided with user feedback, for example if the system is unable to retrieve answers confidently.

Preferably, the method actively learns from user interactions. For example, every interaction of a user with the system may be fed back as a way of retraining classification models which improves accuracy as a number of interactions increases.

The correlation is preferably provided using AI algorithms, which may comprise a Long Short-Term Memory (LSTM) algorithm implemented by a Bi-directional Recurrent Neural network.

Preferably, the AI algorithms form a high-level classifier and a low-level classifier. This provides for more accurate and efficient classification. It will be appreciated that a number of classification models may be combined to provide answers accurately. This may consist of a number of high-level classifiers and several classifiers at a lower-level to each of the high-level classifiers.

Preferably, before receiving the user input, the user input is pre-processed, said pre-processing comprising the steps of tokenizing the user input and vectorising the tokenised user input. This enables capturing descriptive qualities of categorical labels, such as giving similar tokens close numerical representations.

Preferably, providing at least one response comprises providing an avatar video produced according to the first independent aspect. The production of realistic avatar videos enhance user experience whilst the interactive method according to the second independent aspect improves reliability over existing techniques. Accordingly, this combination is synergistic and advantageous over the prior art such using videos which have to be shot using real persons and are therefore often lengthy and expensive to provide. The interactive systems according to aspects of the present invention increase scalability and flexibility of applications.

In a third independent aspect there is provided a system for producing an avatar video, the method comprising the steps of:
  an image processing model for receiving a reference image of a person's face and for extracting a plurality of characteristic features representative of a facial model X0 of the person's face, the characteristic features defining a facial pose dependent on the person speaking;
  a speech processing module for extracting a target phrase to be rendered over a predetermined time period during the avatar video and for providing a plurality of time intervals t within the predetermined time period;
  the speech processing module configured to generate, for each of said time intervals t, speech features from the target phrase, to provide a sequence of speech features; and
  an avatar rendering module for generating, using the plurality of characteristic features and sequence of speech features, a sequence of facial models Xt for each of said time intervals t.

Advantageously, the image processing module and speech processing module are separated. This separation provides advantages in both performance and maintenance.

Preferably, the avatar rendering module is configured to represent physical dynamics of the speech features by solving a system of ordinary differential equations (ODEs). This models realistic head movement.

Preferably, the physical dynamics of speech are represented with a neural network In a fourth independent aspect, there is provided an interactive system (also referred to as an information retrieval system) for providing an answer to a user, the system comprising:
  a database comprising an indexed question library and a plurality of responses;
  a processing module for providing a correlation between the indexed question library and the plurality of responses;
  input means for receiving a question from the user as user input;
  wherein the processing module is configured to search keyword information in the indexed question library based on the user input; and
  providing at least one response to the user based on said correlation.

Preferably, the plurality of responses comprise at least one avatar video produced using a system according to the third independent aspect. The avatar is presented to the user, therefore the user is provided with accurate information visually. Users may interact with the system via a mobile, or PC for example, In a dependent aspect, a healthcare information system comprises an interactive system according to the fourth independent aspect. With a growing amount of data, the healthcare information system enables searching and getting relevant information quickly and accurately. A health question received from a user is processed and developed by the interactive system to fetch the related information from the database; this information is then converted to an avatar video to enhance user experience.

Dependent aspects of each of the independent aspects are provided in the dependent claims.

Particularly when taken in combination, aspects of the present invention can provide more reliable, accurate systems which, at the same time, are visual (video realistic), interactive, personal and contextual to enhance user experience.

In a comparative example, there is provided a method for providing an answer to a user related to a healthcare issue, the method comprising the steps of:
providing a database comprising an indexed symptoms library and a plurality of responses;
providing a correlation between the indexed symptoms library and the plurality of responses; receiving user input related to the healthcare issue; searching keyword information in the indexed symptoms library based on the user input; and providing at least one response to the user based on said correlation.

In a subsidiary aspect, the method further comprises the steps of:
receiving further user input in response to the at least one response provided to the user; and based on the further input, searching further keyword information in the indexed symptoms library; and providing at least one further response to the user based on said correlation.

In a subsidiary aspect, the correlation comprises at least one AI/machine learning algorithm. In a subsidiary aspect, at least one response includes video or avatar implementation. For example, the avatar may be a realistic video representation of a GP which may be created on the fly from a database of information or combining multiple databases of information.

BRIEF DESCRIPTION OF THE SEVERAL VIEWS OF THE DRAWINGS

The disclosure will now be described with reference to and as illustrated by the accompanying drawings in which:

FIGS. 2, 3A, and 3B outline examples of interactive health care systems with machine learning and avatar capabilities;

DETAILED DESCRIPTION OF SPECIFIC EMBODIMENTS OF THE INVENTION

Interactive Systems and Methods

Figure 1:
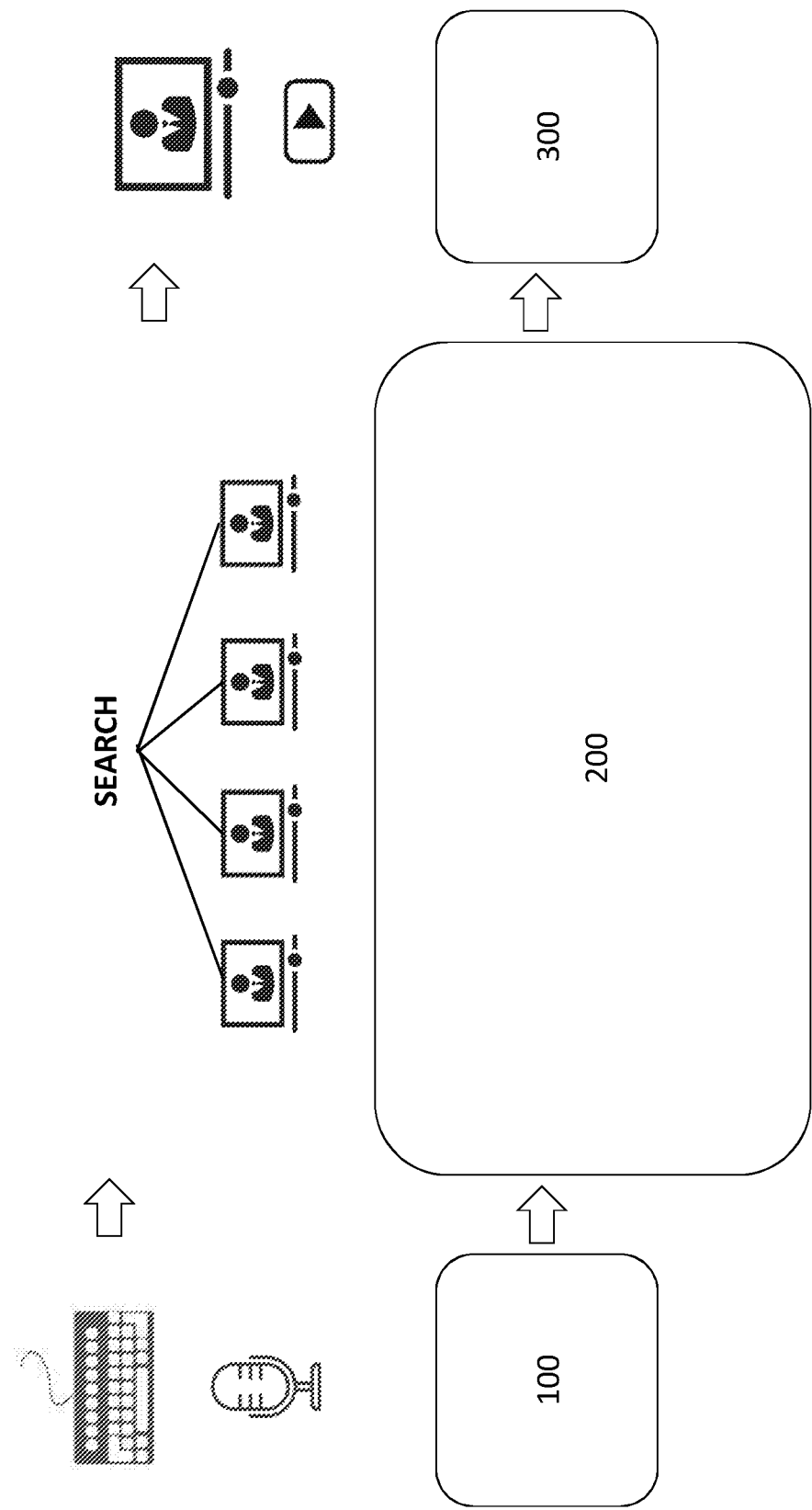
FIG. 1 shows a comparative example of an interactive health care system.

FIG. 1 shows a first example, wherein a user query 100 is input by a user via text or voice. The query may be a question, for example, about a symptom such as cough or sore throat, or about conditions such as coughs or flu. The input is submitted to a digital platform 200 which incorporates a library of answers, in this example, videos featuring a GP which provides answers. Each video may be on a particular health topic, has associated keywords, and can be searched and output contextually as an answer 300 to the query 100 submitted. Although videos are preferred, it will be appreciated that the library of answers as well as output may have other suitable formats, including text, images, etc. It will also be appreciated that the length of the videos may vary from topic to topic.

In this example, the search is an "elastic search" (https://en(dot)wikipedia(dot)org/wiki/Elasticsearch). Advantageously, an elastic search is distributed, providing a scalable, near real-time search. Each video is indexed and tagged with keyword tags relevant to the health topic they address. The search accuracy may be improved by including a function for determining synonyms of the keywords in addition to the assigned keywords themselves.

Figure 2:
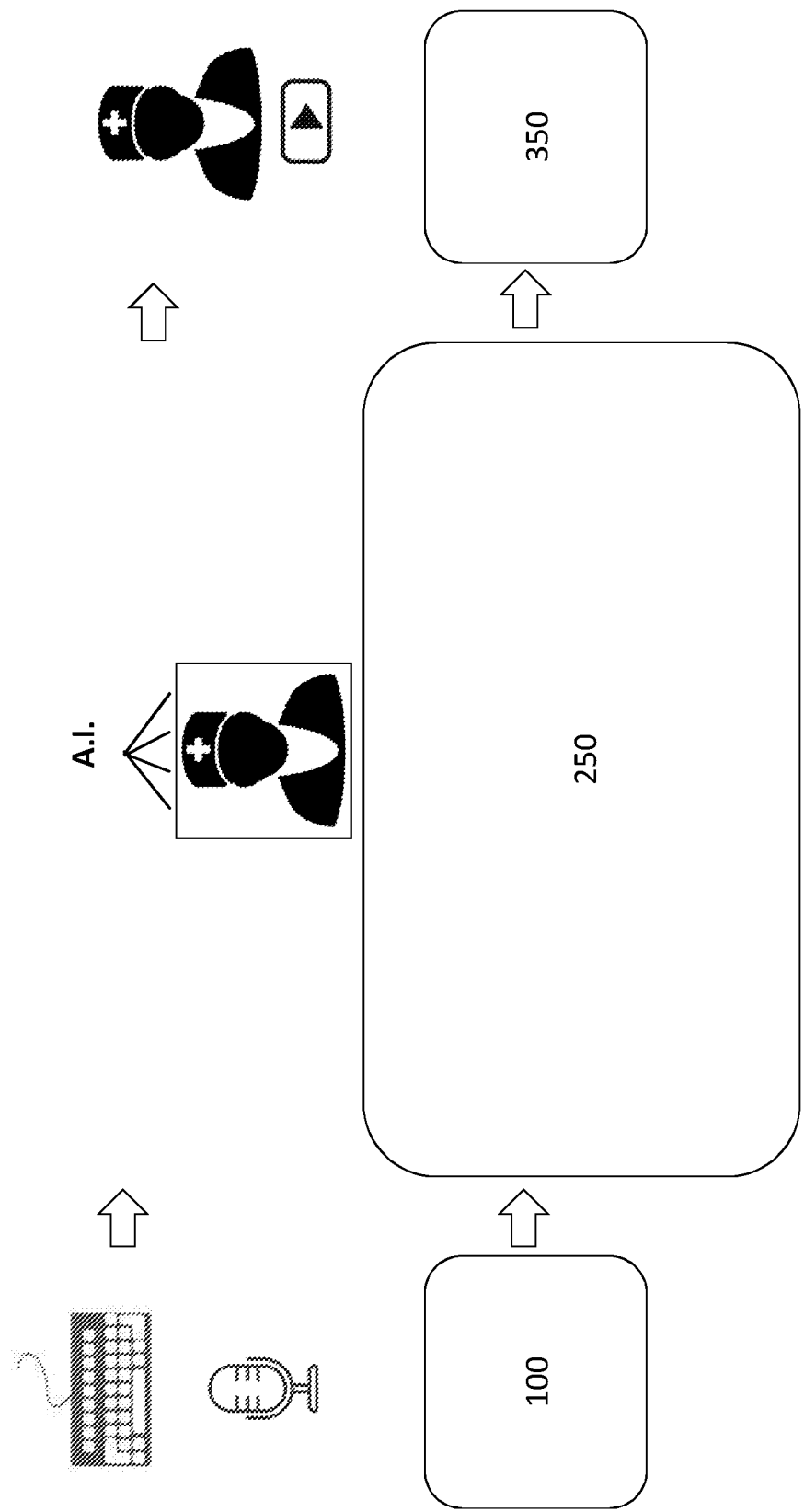

FIG. 2 shows a second example, wherein the user query 100 is input by a user via text or voice. In this example, the digital platform is an artificial intelligence (AI) platform 250 and outputs 350 are provided via a video or video realistic avatar sequence to provide a response to the submitted queries. Machine learning techniques are employed for the AI platform 250 to learn from user feedback training and thus to provide increasingly accurate responses over time. Particular applications envisaged include education of patients, chatbots for answering sexual health-related problems, and prediction of the likelihood of heart problems and back pain diagnostics.

In a preferred scenario, an avatar is presented to the user, prompting the user to ask their question(s). The user input 100 may be either spoken (via a microphone) or written. The system then converts the spoken or written sentences to high dimensional vector representations of the user input 100. This is done through neural architectures such as 'word2vec' ('https://papers(dot)nips(dot)cc/paper/5021-distributed-representations-of-words-and-phrases-and-their-compositionality(dot)pdf) or 'glove' (https://nlp(dot)stanford(dot)edu/pubs/glove(dot)pdf) where the words having similar syntactical and semantic features are placed in proximity. The high dimensional representations of the user input 100 are used by the system to interrogate a symptoms database for example. A set of initial results is generated.

Next, an output in the form of an avatar video is fetched (or generated) based on the set of initial results. The output may include a question to the user to request further information based on the set of initial results if the AI has low confidence on initial results. Accordingly, the system is interactive and iterative. That is, the system continues to extract useful information from successive user inputs and uses this to interrogate the database in order to generate further, secondary queries and smaller, consecutive results subsets from the initial results set, until a single result or small enough subset of results with high confidence is arrived at. This may include a complete re-set so as to generate a fresh/new set of initial results if the subsequent user responses render this as necessary (e.g. if subsequent queries provide a null/empty subset).

In an example, avatar image sequences are generated offline, in non-real-time, for a given text or audio speech target. This process requires storing a number of similar reference frames to be used to generate the output sequence. More frames provide greater temporal coherence and video quality at the expense of increased computation.

In an alternative, preferred example, avatar sequences are generated on the fly. On the fly generation aims to generate video in real-time from only a single reference image and a known sequence of speech labels, provided as encoded audio sequences or from the text databases of information. The system also incorporates an active learning schema which learns actively based on the history of user inputs and AI responses, improving the AI's confidence to answer a user query/input continuously over time.

Preferred, but non-essential system capabilities include voice recognition, avatar personalisation (including voice/ dialect personalisation) and personalisation/results focusing taking into account a user's preference or medical history.

With reference to FIG. 3A, the user query 100 is input by a user via text or voice. AI algorithms are implemented in a digital platform 270, which is faster, scalable and more reliable than elastic search techniques. The output 370 may be in any form, for example, provided on a computer screen, smartphone or tablet.

Preferably, the output 370 is in the form of concise, relevant answers within an avatar video. With reference to FIG. 3B, the avatar in this example is produced with an avatar sequence generator 40 using text databases and audio data. Preferably, the avatar sequence generator 40 has capabilities of 'on the fly' sequence generation. This incorporates a number of features including real-time functionality, single reference image of targets, multi-format speech targets (text or audio) and the ability to generate footage from previously unseen targets.

The AI algorithm improves reliability over existing techniques, whilst the video realistic avatar enhances user experience. This is advantageous to using videos which must be shot using real persons and are therefore often lengthy and expensive to provide. Using avatars increases scalability and flexibility of applications.

Production of Speech Driven, Audio-Visual Avatars

The present section describes systems and methods according to aspects of the invention, used to create a digital avatar, using audio-visual processing for facial synthesis. From these, a database of digital avatars may be built to be used in the examples of interactive systems and methods provided above, and as will be further described with reference to FIG. 9 below.

Advantageously, an interactive user interface may be therefore provided to a specialised chatbot that can answer healthcare questions. It will be appreciated, however, that the described systems and methods can also be used in standalone audio-visual processing algorithms for facial synthesis. The methods make use of modern machine learning and digital signal processing techniques.

The purpose of this aspect of the invention is to create 3-D facial models of a target subject (e.g. a doctor or nurse which a user may already be familiar with) to produce a hyper-realistic speech driven avatar of that target subject. In preferred embodiments, given a target phrase recorded as spoken by the target subject and reference appearance (e.g. an image of the subject), the system will provide videos of the target subject speaking the target phrase.

Figure 4:
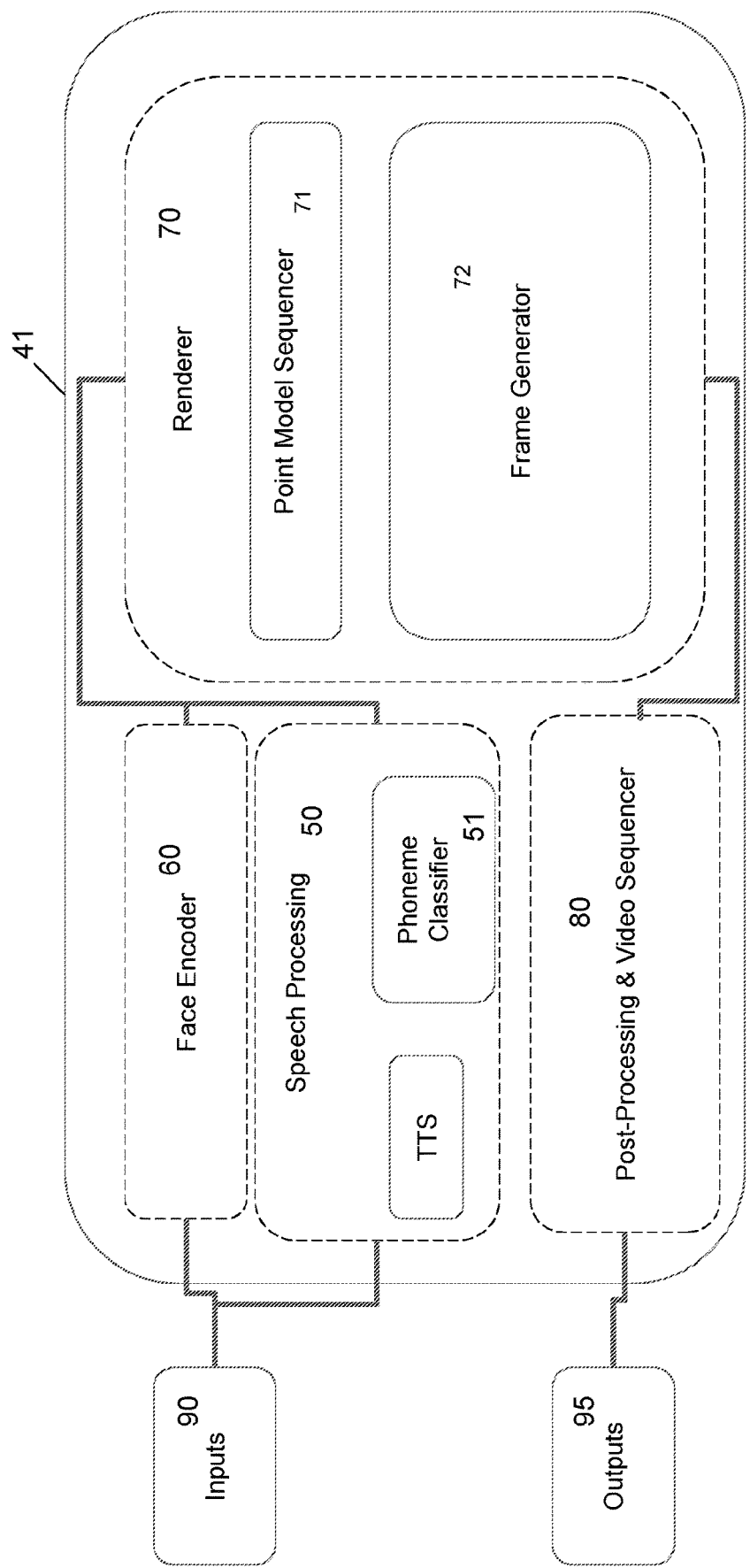
FIG. 4 shows a system for producing a speech-driven audio-video avatar according to an aspect of the present invention (high-level descriptor of a dual network system)

With reference to FIG. 4, a system 41 for creating an avatar video comprises a plurality of modules (modular sub-systems), including: a speech processing module 50, an image processing module ('face encoder') 60, a frame rendering ('avatar rendering') module 70 and a post-processing and video sequencer module 80. The speech processing module 50 and the image processing module ('face encoder') 60 are separate—this separation is important as it provides advantages in both performance and maintenance.

The modular design of the system 41 enables the system to be operable in several configurations (modes), for example for online and offline usage. In offline mode photorealism and synchronicity are prioritised whereas online mode aims to achieve light-functionality to support mobile devices and video-streaming. Advantageously, the system 41 may be provided as a service platform, e.g. in combination with a digital platform 270/AI engine 280 as outlined in FIG. 3A and FIG. 9, respectively, or as a stand-alone application (e.g. a plug-in).

Each module of system 41 comprises data pathway (data flow) and specialised processing. FIG. 4 shows the overall data-flow as well as the I/O interface points (inputs 90 and outputs 95). Inputs 90 may include a reference appearance model of a target subject face (target face) which is a 3-D face model for example or a face image. Inputs 90 may also include a target phrase, which may be provided in any suitable form such as text or raw audio data.

The image processing module 60 is configured to extract a plurality of key descriptive parameters (descriptors) from the reference model of the target face (the 'reference image'). The descriptive parameters may include characteristic features referred to as landmark points (landmarks) known from Active Shape Models (ASMs), as well as latent descriptors (vectors) representing abstract appearance features (such as colour, texture etc.). ASMs are statistical models of the shape of objects which iteratively deform to fit to an example of the object in a new image. The latent descriptors may be extracted using a pre-trained Deep Convolutional Network (DCN).

In alternative embodiments, where no reference appearance model is supplied (e.g. as a reference face image), pre-extracted parameters may be used instead, as available. Advantageously, subjective appearance features may thus be separated from general shape features which is dependent on speech (as changing whilst the target face is speaking).

Historically the parameters used are the location of keypoints such as mouth corners, nose edges, etc. In existing parametric models, such as ASMs these are compressed with Principal Component Analysis (PCA) to reduce the dimensionality and standardize representations. The PCA encoded features can then be clustered into distinct modes (i.e. most frequent/dense distributions). These modes of variation capture common expressions and poses. The advantages of this approach are efficiency and relatively low computational time. The disadvantages of this approach are that each model is subjective, requiring large amounts of very similar data for accurate reconstruction, and that rendering new images from point models requires a separate process.

Active Appearance Models (AAMs) attempt to resolve this by parametrising texture maps of the image, however this a limiting factor. In contrast, the fully data-driven approach common in modern computer vision does not attempt to parameterise the subject model and instead is focused on producing images from the offset. This involves learning how pixels are typically distributed in an image. As such, the features are learned directly from the images and are more abstract—typically in the form of edges and gradients that describe low-level image data. A disadvantage is that these models are highly specific to the training task and may function unpredictably to new data. Further restrictions include a need to fix image resolution.

The speech processing model 50 receives an input target phrase. The input target phrase may be generated (e.g. by a chatbot backend) using Natural Language Processing. Alternatively, the input target phrase may be specified by a user.

This input target phrase 90 may be supplied as a text input and/or audio waveform for example. Where no audio recording is available the target phrase may be generated with Text-To-Speech (TTS) software. From the audio waveform, phoneme labels are preferably generated, with a phonetic classifier module 51, at pre-set time intervals—this advantageously provides a phoneme label for each video frame. A phoneme label (also referred to as a phonetic label) is a type of class label indicating fundamental sounds common in speech.

From the input target phrase, the speech processing model 50 extracts speech features and, optionally, phoneme labels. Speech features are defined as abstract quantifiers of audio information such as, but not limited to, short-time-frequency representations i.e. mel-frequency cepstral coefficients (MFCCs), per-frame local energy, delta coefficients, zero-cross rate etc.

An avatar rendering module 70 receives the extracted descriptive parameters from the image processing module 60 (which include landmarks) and the extracted speech features and phonetic labels from the speech processing module 50. The avatar rendering module 70 comprises a point model sequencer 71 which receives the descriptive parameters (point model) from the from the image processing module 60 and the extracted speech features and phonetic labels from the speech processing module 50.

The point model sequencer 71 preferably uses a recursive model ('pose-point model') to generate a sequence of landmarks giving the face position and pose at each time interval of the avatar video. A 'pose' refers to both the high-level positional information i.e. gaze direction, head alignment, as well as capturing specific facial features and expression. The recursive model is preferably based on Long Short-Term Memory networks (LSTMs), which are known as a special type of recurrent neural networks comprising internal contextual state cells that act as long-term or short-term memory cells. The output of the LSTM network is modulated by the state of these cells. This is an advantageous property when the prediction of the neural network is to depend on the historical context of inputs, rather than only on the very last input.

The avatar rendering module 70 further comprises a frame generating model 72 ('frame generator') which receives the output of the point model sequencer 71, that is, the sequence of landmarks giving the face position and pose at each time interval of the avatar video—additionally we colour code high level semantic regions such as lips, eyes, hair etc. The frame generator renders these into full frames using a specialised style-transfer architecture (as will be described below with reference to FIG. 8).

System 41 further comprises a post-processing and video sequencer module 80 which receives the generated frames from the frame generator 72 of the avatar rendering module 70. Following 'light' post-processing such as image and temporal smoothing, colour correction, etc, module 80 encodes these frames together with a target audio input into an avatar video. The target audio input provided to the module 80 may be supplied or generated. In an example, the 'Text-To-Speech' capability of the speech processing module 50 is used to supply the target audio input to the module 80.

Figure 5:
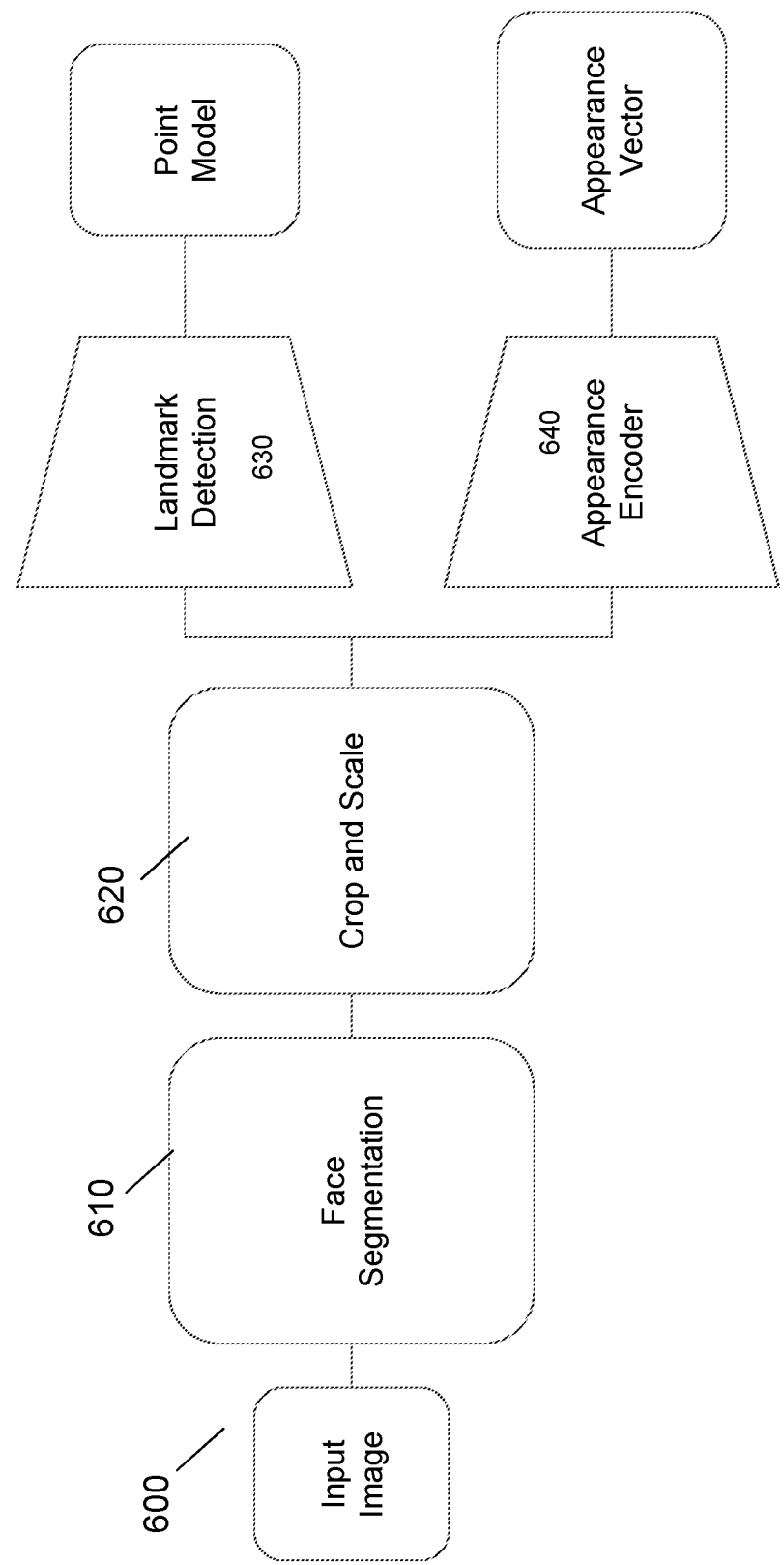
FIG. 5 shows a method of extracting point model and appearance features of a given face image.

Turning to FIG. 5, an exemplary method used by the face encoder 60 is illustrated. At step 600, a face is identified with an image, using for example a pre-trained DCN. At step 610, the identified face image is segmented using a binary mask. The binary mask advantageously removes background from the face image, which reduces variance during training, therefore providing for a more accurate identification of the faces. At step 620, the segmented image is cropped and scaled to a predetermined size.

At step 630, a landmark detector DCN extracts landmark points (landmarks) from the image out at step 620, which represent key parameters. This provides the point model to be input to the point model sequencer 71 of the avatar rendering module 70.

Separately (in parallel to step 630), an appearance encoder network is used, at step 640, to encode the image appearance features as an appearance vector. The appearance vector is input to the frame generator module 72 of the avatar rendering module 70.

Figure 6:
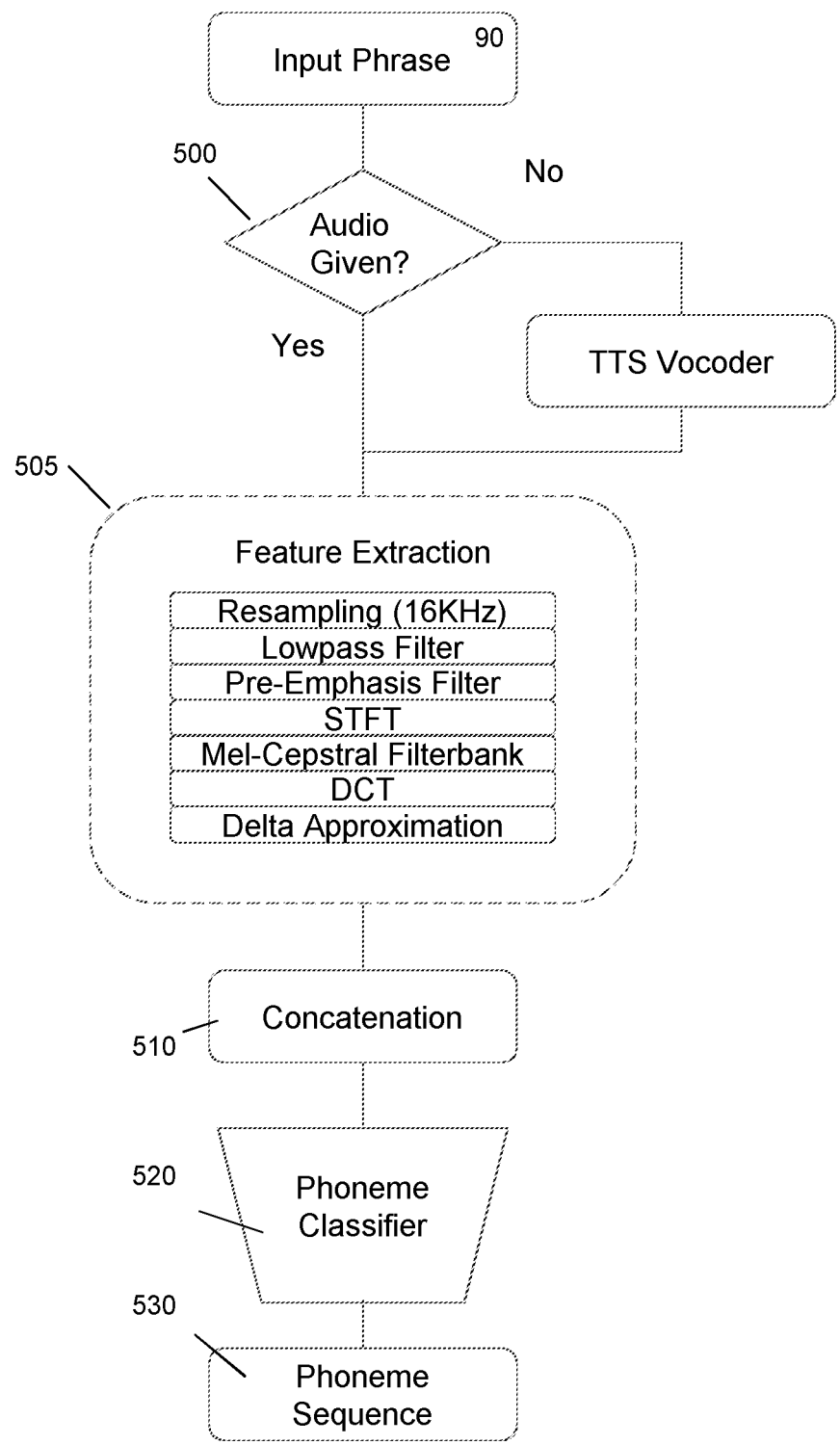
FIG. 6 shows a speech processing method including steps for feature extraction.

Turning to FIG. 6, an exemplary method used by the speech processing module 50 is illustrated. At step 500, the module checks if the input target phrase 90 includes audio data. If the input 90 contains no audio, but it contains only text input instead, a Text-To-Speech (TTS) encoder may be used to produce a waveform specified by the user query. It will be appreciated by the skilled person that there are many envisaged ways of producing the audio data, such as vocoders, concatenated speech, and fully generative methods such as Wavenet.

At step 510, feature extraction is performed using a speech classification algorithm as shown in FIG. 6. In this sequential pipeline pre-processing example, post-processing and feature extraction are combined (steps 505).

At steps 505, the audio input 90 is first re-sampled for example by decimation or frequency based interpolation to a fixed frame rate of 16 KHz. Following this, the signal is passed through an anti-aliasing filter (e.g. with 8 Khz cut-off). Pre-emphasis is performed for example with a simple high-pass filter to amplify higher frequencies better descriptive of speech. Finally, the signal is rms normalised and separated into short time frames synchronised to the video frame rate.

The feature extraction processing involves discrete Fourier transforms on these frames to obtain a spectrogram. The per-frame energy is extracted here. As the frequency is logarithmically scaled, higher frequencies are less impactful and as such can be grouped into energy bands. This is the inspiration behind the mel-cepstral spectrogram, wherein a filter bank is used to group frequencies into increasingly wider bands. This severely reduces dimensionality and increases robustness. The mel-frequencies are then passed through a discrete-cosine-transform (DCT-II) to provide the MFCCs. Post-processing can then be applied per-speaker to transform each feature to a normally distributed variable.

In this example, the speech classification algorithm is used to extract mel-frequency cepstral coefficient (MFCC) audio features and the time derivatives are linearly approximated with a 2nd order symmetric process. These features are then concatenated, at step 510, to give a local contextual window containing the speech features from time steps either side of the specific frame. This has the benefit of increasing the scope of each frame.

At step 520, phonetic labels are generated with the phonetic classifier module 51. In an example, a 1D Convolutional Network is used to provide "softmax" classifications of the predicted phoneme. This uses an autoencoder to predict the probability distribution across the phonetic labels for a given set of speech features. In addition, Bayesian inference may be applied by modelling a prior distribution of likely phonemes from the text-annotation to improve performance. At step 530, the output of this Network is a sequence of phoneme labels $\{P_0, \ldots P_t, \ldots P_N\}$ for each video frame interval.

Figure 7:
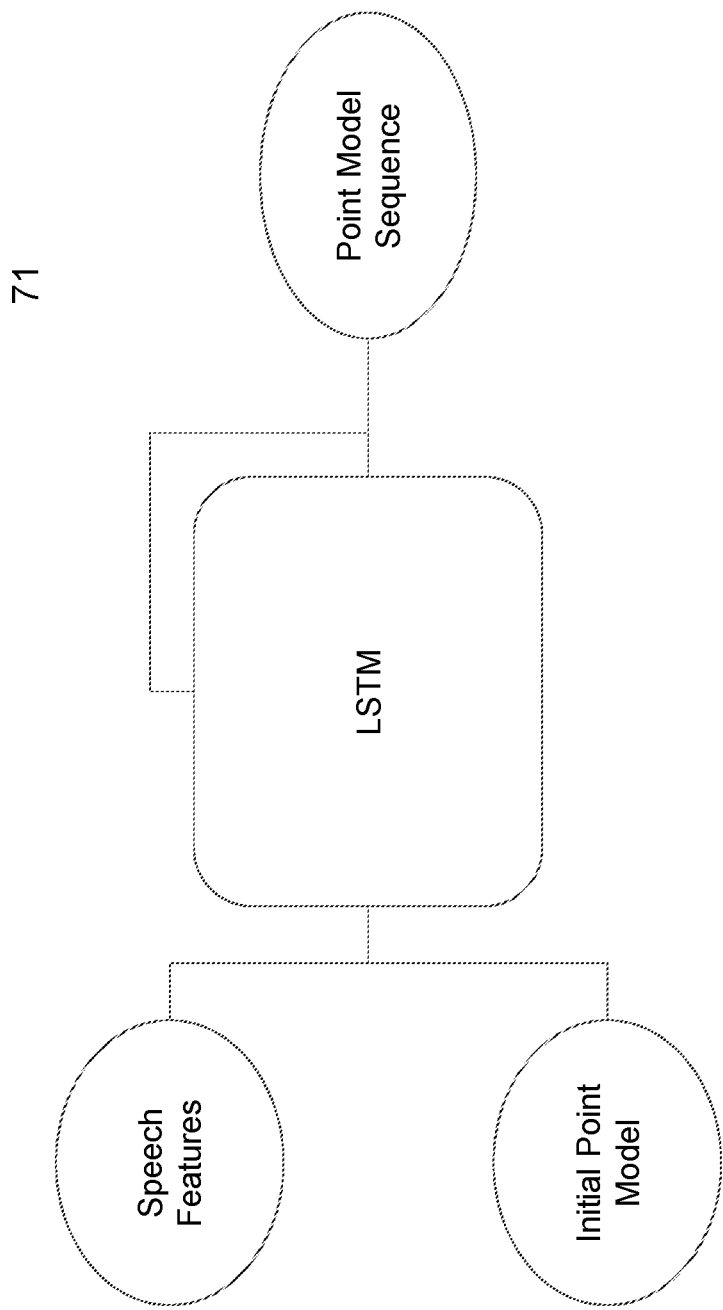
FIG. 7 shows a sequential point-model generator used to model the dynamics in head and mouth movement during speech.

Turning to FIG. 7, a method to be carried out by the point model sequencer 71 is illustrated. The point model sequencer 71 receives the phoneme labels sequence $\{P_0, \ldots P_t \ldots P_N\}$ and an initial face pose model X0 and generates face pose models $X_t$ for each frame at time t. The point model sequencer 71 uses a recursive model preferably based on Long Short-Term Memory networks (LSTMs). In effect this is an application of sequence-to-sequence ("seq2seq") encoder decoder framework and as such a bi-directional LSTM is a preferred implementation. The output of the point model sequencer 71 is thus a sequence of face pose models $X_t$ per each frame, which represents framewise positional information.

Figure 8:
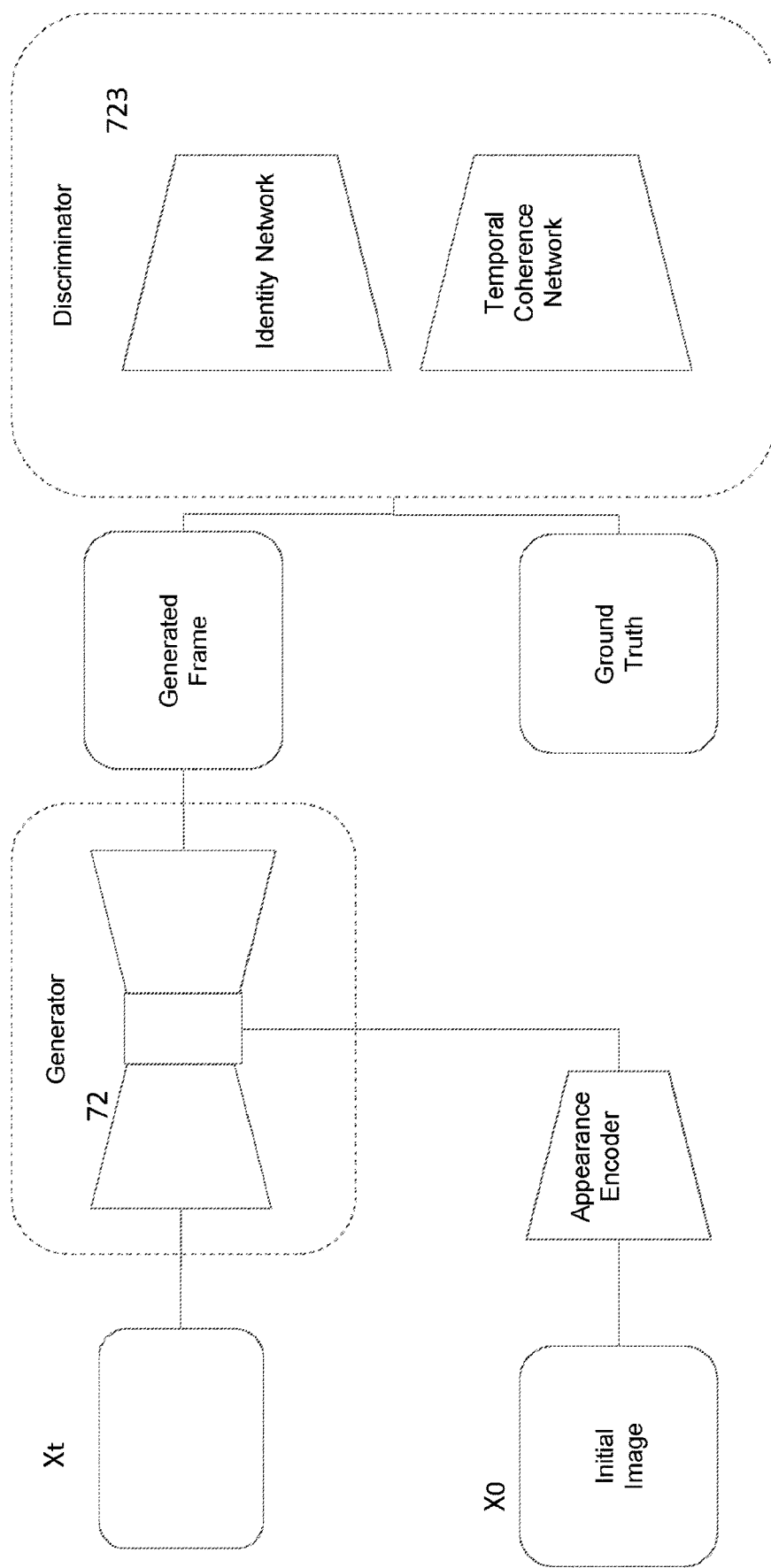
FIG. 8 shows a style-transfer network used to render images with the appearance of a reference image and pose content from the generated point model representation.

Turning to FIG. 8, a method to be carried out by the frame generator 72 is illustrated. Each of the face pose models $X_t$ is input into the frame generator 72 to be combined with the initial face pose model X0 (reference appearance model) and produce full frames. This may be achieved with a discriminator sub-module 723 specialised style transfer architecture, that uses specialised loss functions and discriminator networks. Specifically, the aim is to minimise the difference between appearance encodings of difference frames of the same subject.

Advantageously, a generalised face discriminator ensures realism. A face-discriminator takes single colour images and detects realism. Furthermore, a temporal coherence network may be used to score the neighbouring frames and pose errors. A temporal discriminator is a 2D convolutional encoder that takes a sequence of grayscale images stacked in the channel axis to score the relative temporal consistency. As such, this detects inconsistent movements between frames.

FIGS. 14 to 17 illustrate a further system 4100 for producing hyper-realistic and responsive avatar videos according to another aspect of the present invention. The system 4100 may be an independent component (module) capable of producing a video realistic and responsive avatar to engage users interactively. The system 4100 combines the strengths of physical models and neural network approaches.

Figure 14:
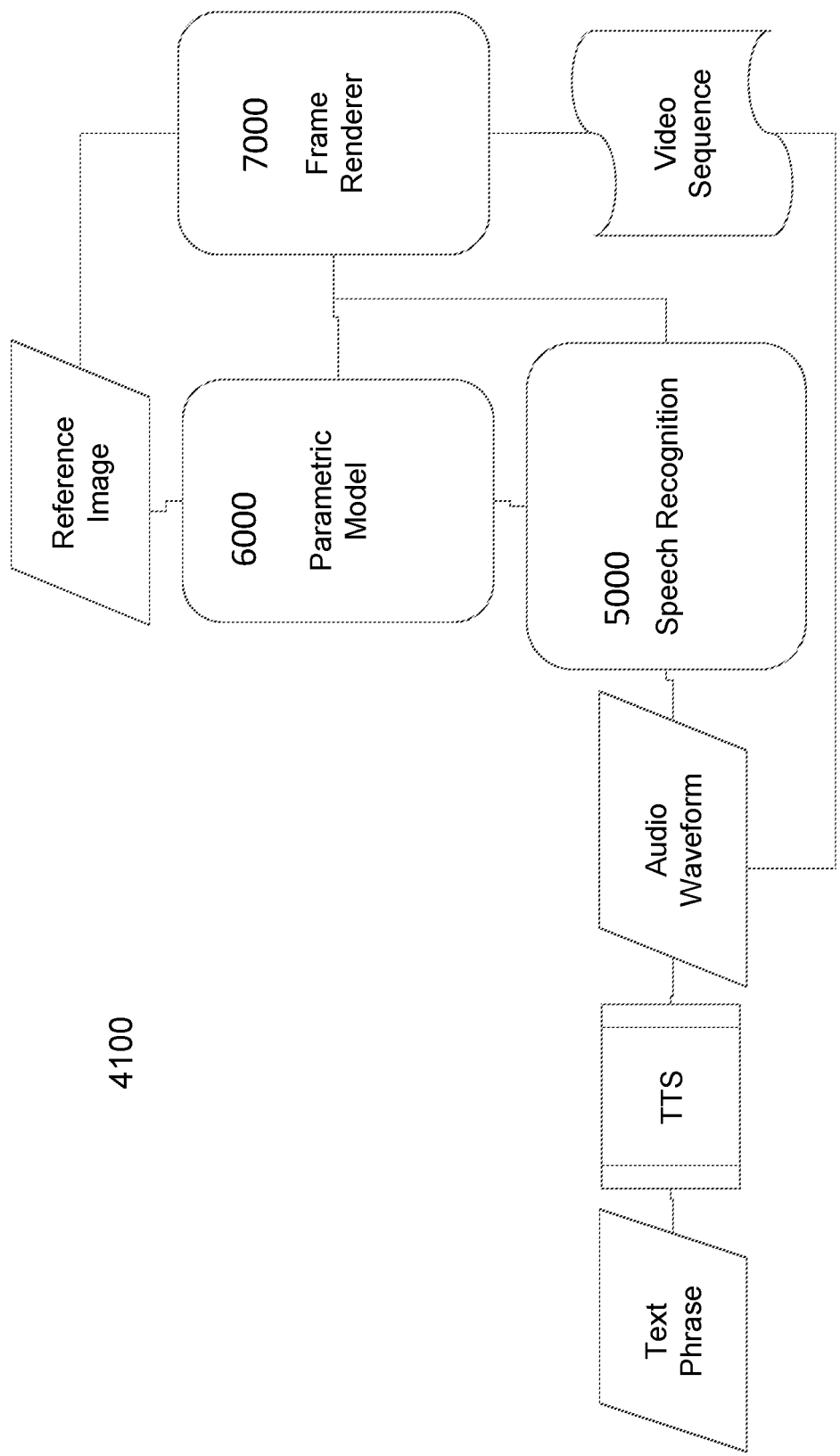
FIGS. 14, 15, 16 and 17 illustrate a further system for producing hyper-realistic and responsive avatars according to another aspect of the present invention.

FIG. 14 is a schematic block diagram of system 4100 which comprises three main modules: an image processing module ('parametric model module') 6000, a speech processing ('Automatic Speech Recognition (ASR)') module 5000 and a frame rendering module ('frame renderer') 7000. The inputs to the system in this example are a single reference image and an arbitrary length mono audio waveform of the speech to be given. Alternatively, the system can use a text response by incorporating a text-to-speech (TTS) module such as the WORLD Vocoder, Tacotron, AWS TTS etc. The output is a video sequence of the avatar speaking the query phrase.

Figure 15:
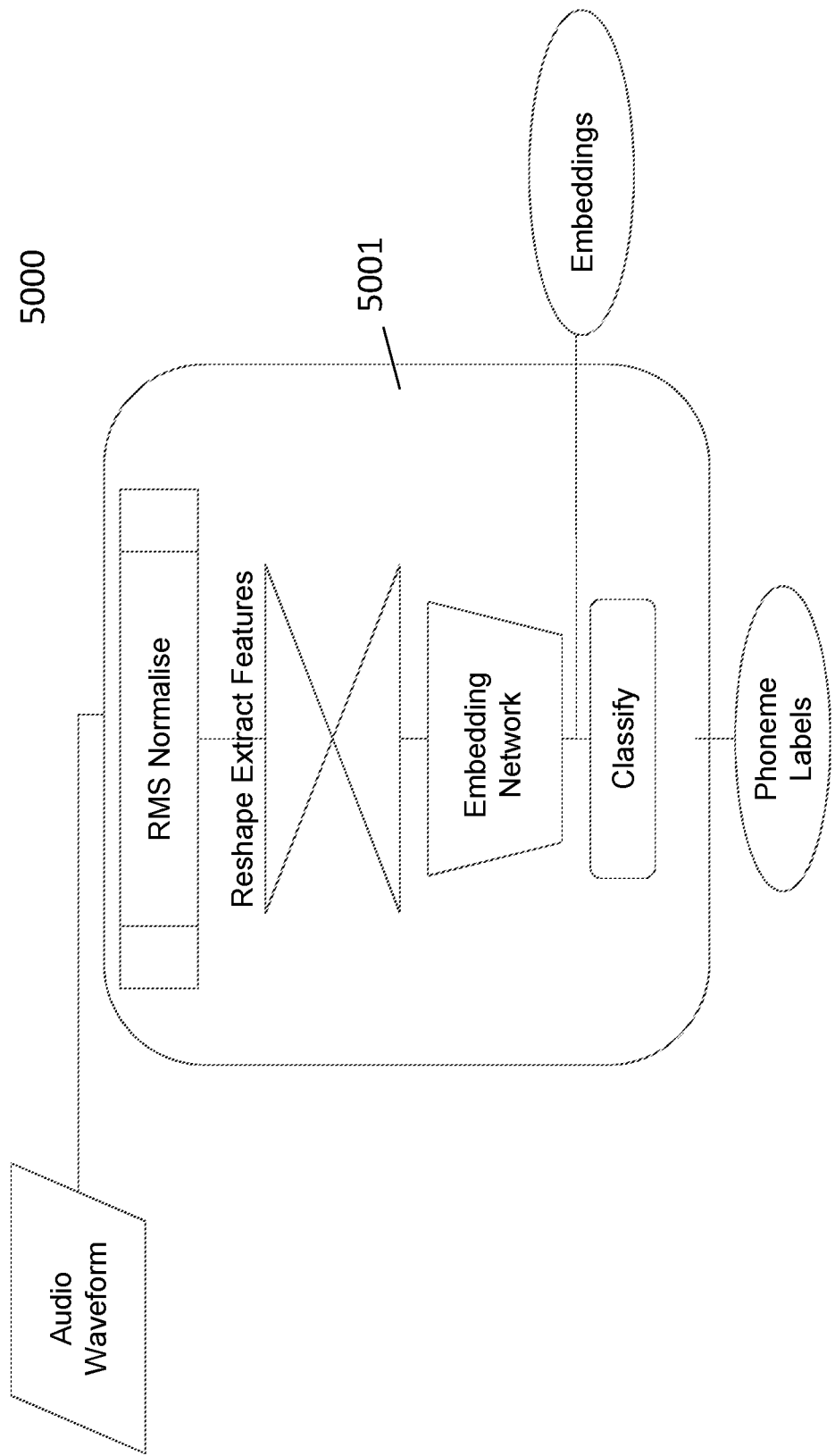
Figure 16:
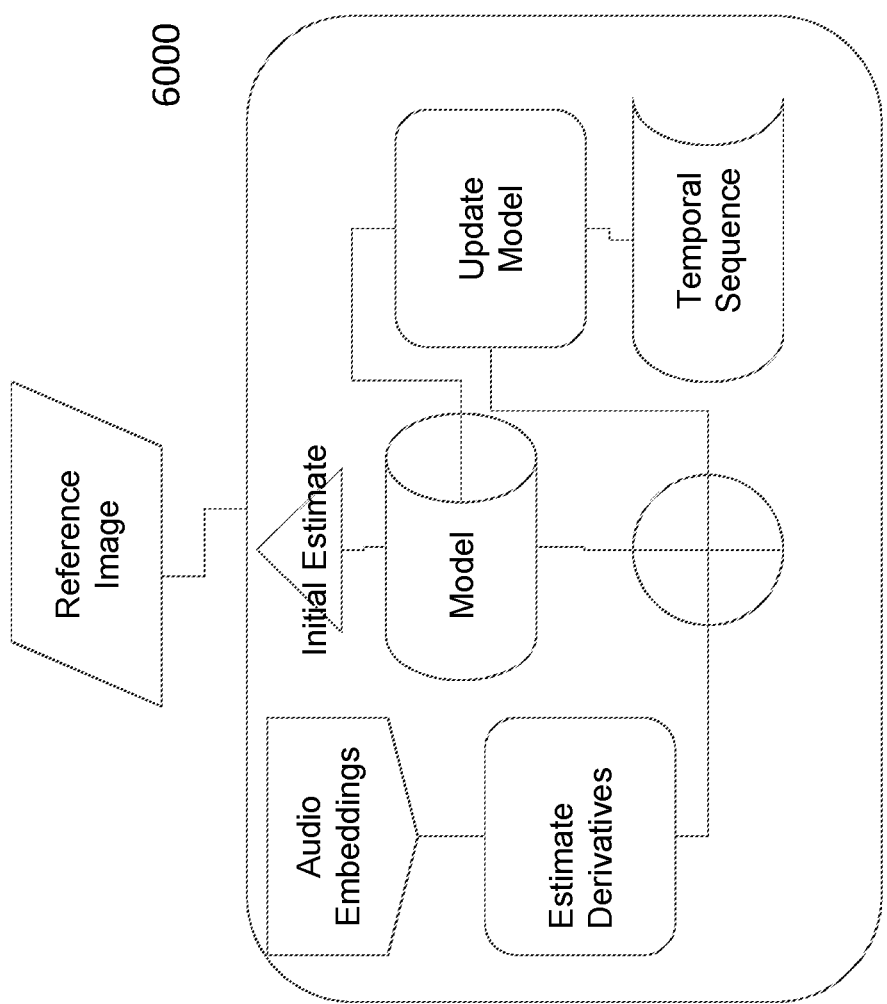

The speech recognition module 5000 transforms the audio input into a sequence of descriptors in a multi-stage sequence as exemplified in FIG. 15. First, the audio input in this example is normalised to a predefined rms power and divided into equally spaced frames at intervals of time t. From these frames, features descriptive of speech are extracted, such as MFCCs, i-vectors, instantaneous fundamental frequency, etc. These descriptive features are preferably standardised to equivalent scales. Features from concatenated frames over a short temporal window are fed as inputs to a specialised convolutional recurrent encoder for example, where they are embedded into a latent space to produce a sequence of embeddings. These embeddings are used by both the parametric model 6000 and in a phoneme level classifier 5001 to produce a sequence of per-frame phoneme labels.

The parametric model module 6000 is a temporal version of the physical models used in AAMs and similar. We estimate both a descriptive physical representation and the temporal dynamics as a function of speech. The process employed by the parametric model 6000 is outlined with reference to FIG. 16.

The parametric model 6000 represents the physical dynamics of speech with a first order Ordinary Differential Equation (ODE). This allows the position of face vertices to change in response to speech. In the data flow an initial estimate is first extracted from a reference image—while not a necessary requirement, it is preferred that the initial image is frontally aligned, well-lit and in a neutral or resting pose. With the speech embeddings from the ASR network, the framewise derivatives for each vertex are estimated such that by adding these derivatives to the current model we arrive at the vertices positions at the next frame. This can be done auto-regressively for arbitrary length sequences at arbitrary frame rates to produce a temporal sequence of face poses and expressions.

Figure 17:
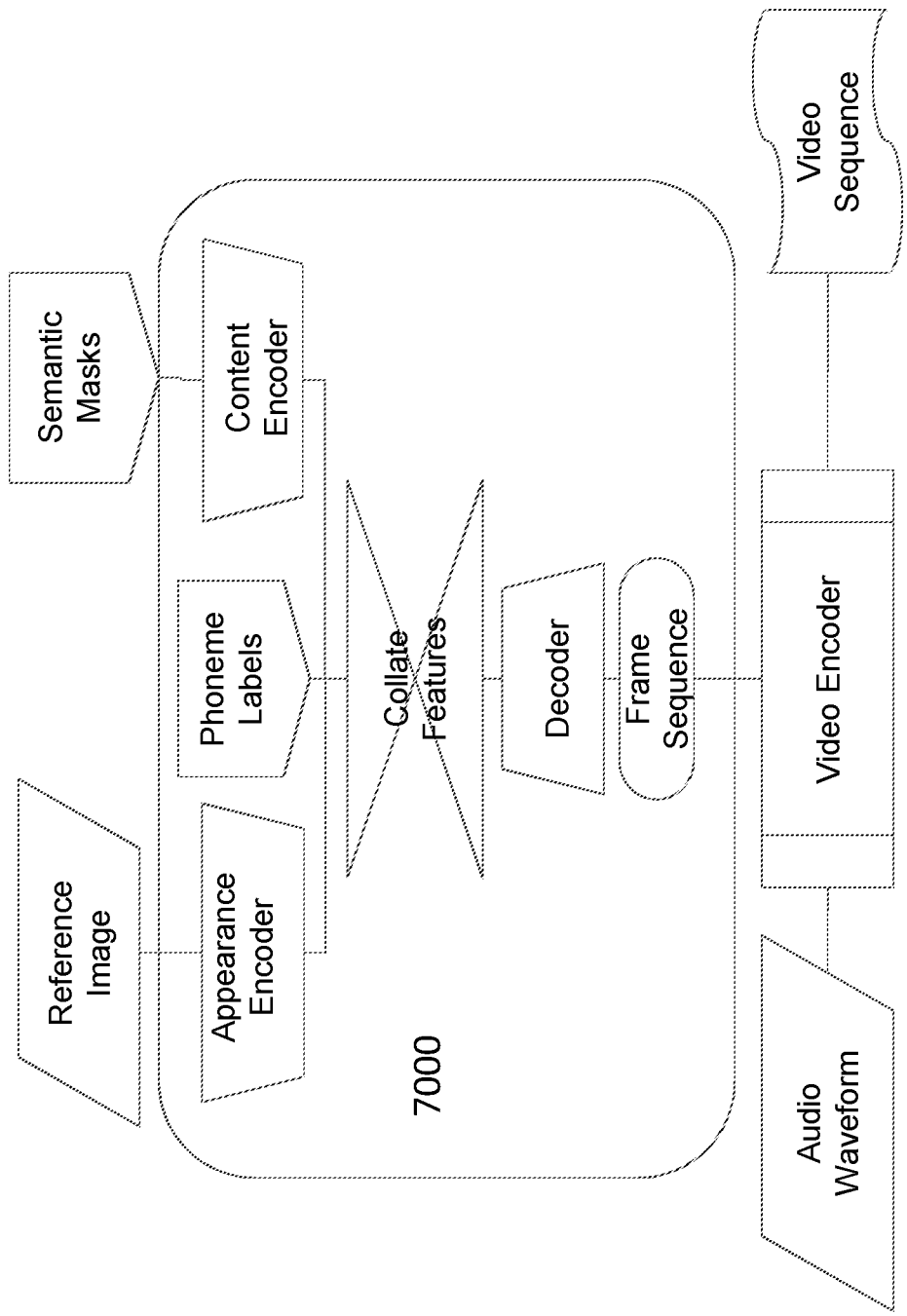

As these physical models do not contain texture maps or high-resolution detail, rendering is done separately, in the frame renderer module 7000 as exemplified in FIG. 17. The rendering module 7000 takes semantic information from the previous modules 5000, 6000 pertaining to face pose, expression and speech content alongside a reference image (as was shown in FIG. 14) and transforms the semantic maps into photorealistic, temporally smooth video frames. Advantageously, the method renders photorealistic images in arbitrary poses, whilst preserving appearance and identity.

It will be appreciated that systems 41, 4100 as described above may be used in stand-alone applications outside healthcare, for example to provide avatars for any virtual environments, video-communications applications, video games, TV productions and advanced man-made user interfaces.

AI Systems and Methods for Interactive Health Care Systems

The present section describes systems and methods according to aspects of the invention for providing an AI module to be used in the examples of interactive systems and methods provided above, and particularly, in combination with the avatar database.

The purpose is to create a system architecture and process that can accurately and quickly answers questions posed by the user in the natural language. Advantageously, an interactive user interface may be therefore provided to a specialised chatbot that can accurately answer healthcare questions by a realistic avatar. The system is referred may be referred to as an 'interactive healthcare system'. It will be appreciated, however, that the described systems and methods can also be used in standalone applications outside healthcare. The systems and methods make use of modern machine learning techniques.

Figure 9:
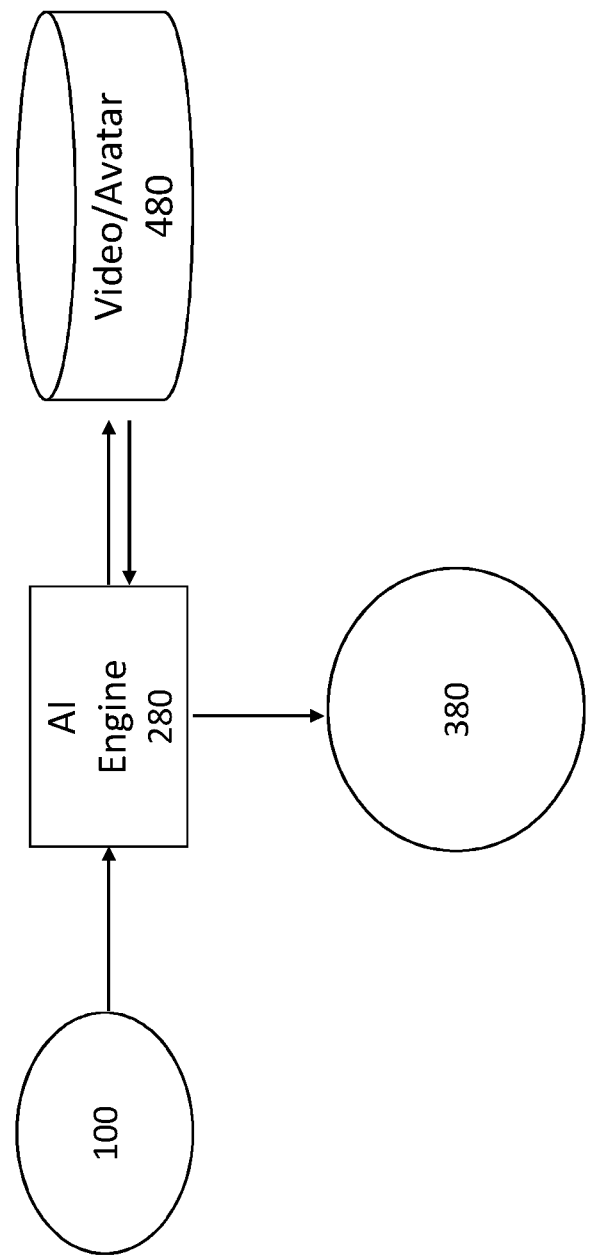
FIG. 9 shows an interactive health-care system according to an aspect of the present invention, including an AI engine and video/avatar database.
Figure 10:
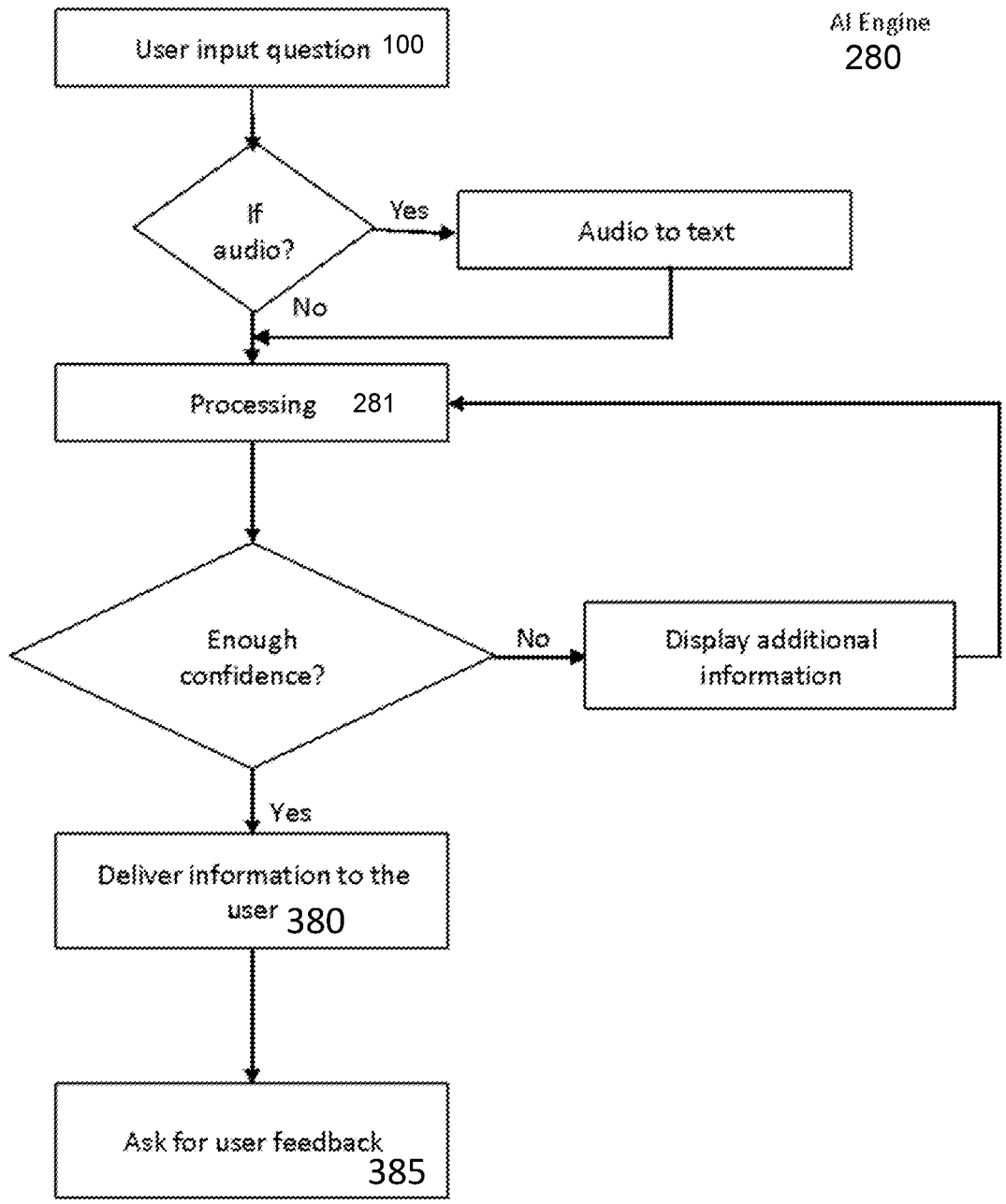
FIG. 10 shows a process employed by sub-modules of the AI engine.

With reference to FIG. 9, an interactive system comprises an AI module 280 ('AI engine') and a database 480 which may include video avatar videos produced with the systems and technique described in the previous section. A user question may be received as an input 100 to the AI module 280 in the form of text or audio data (voice). The AI module 280 processes and analyses the user question and fetches the relevant answer(s) from the video avatar database 480. As will be described in this section, AI algorithms are implemented by the AI module 280, to provide a faster, scalable and more reliable solution than non-machine learning techniques.

The answer(s) fetched from the database 280 may be presented to the user in the form of an output 380 as avatar video, or normal video or text based on availability. Preferably, the output 380 is in the form of concise, relevant answers within a realistic avatar video. The output 380 may be presented in any form, for example, provided on a computer screen, smartphone or tablet.

Turning to FIG. 2 shows a data flow for the AI module 280. Users can use voice and/or text to input a question for example. If the input 100 comprises audio data, then this is converted to text using commercially available audio to text platforms.

The input 100 is then then provided to a processing sub-module 281 of the AI module 280. The processing module 281 processes machine and or deep learning algorithms. Before the input 100 is provided to the machine learning algorithm 281, the input is pre-processed with a pre-processing sub-module 282 (shown in the FIGS. 12 and 13).

Figure 13:
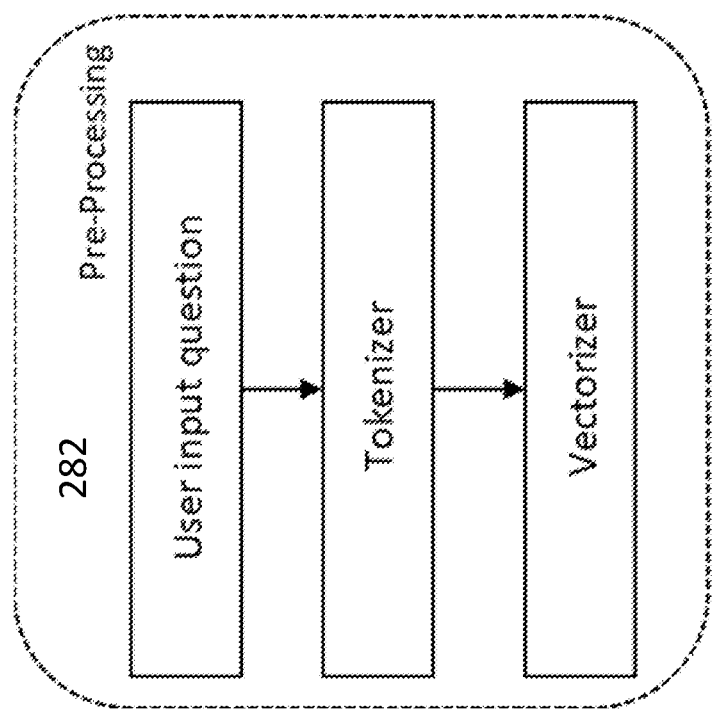
FIG. 13 shows the pre-processing component of the AI engine.

With reference to FIG. 13, the main functionality of the pre-processing module 282 is to divide a question sentence into words, group of words and characters known as tokenisation. Tokenising methods are known—in this example Tensorflow modules have been used to undertake tokenisation. Once the input 100 is tokenised, it is then vectorised using known techniques such as a "word2vec/glove" language model. Vectorisation is a technique used to transform categorical data into enumerated representations. Good vectorisation will capture descriptive qualities of the categorical labels—such as giving similar tokens close numerical representations.

Once pre-processed, the input 100 is then provided to the machine learning algorithm of the processing module 280 for training and prediction. The machine learning algorithm used in this example is "Bi-LSTM" which represents a combination of Long Short-Term Memory (LSTM) and Bi-directional Recurrent Neural Networks (RNNs). As the name suggests, bi-directional RNNs are trained on both the forward and backward bass of a sequence simultaneously. In comparison the bi-directional LSTM is similar but also includes internal passing and forget gates allowing features to pass through long sequences more easily. Bi-LSTM is the special development of artificial neural networks to process sequence and time series data. It will be appreciated that the algorithm used will constantly evolve and that other suitable algorithms may be used.

Figure 12:
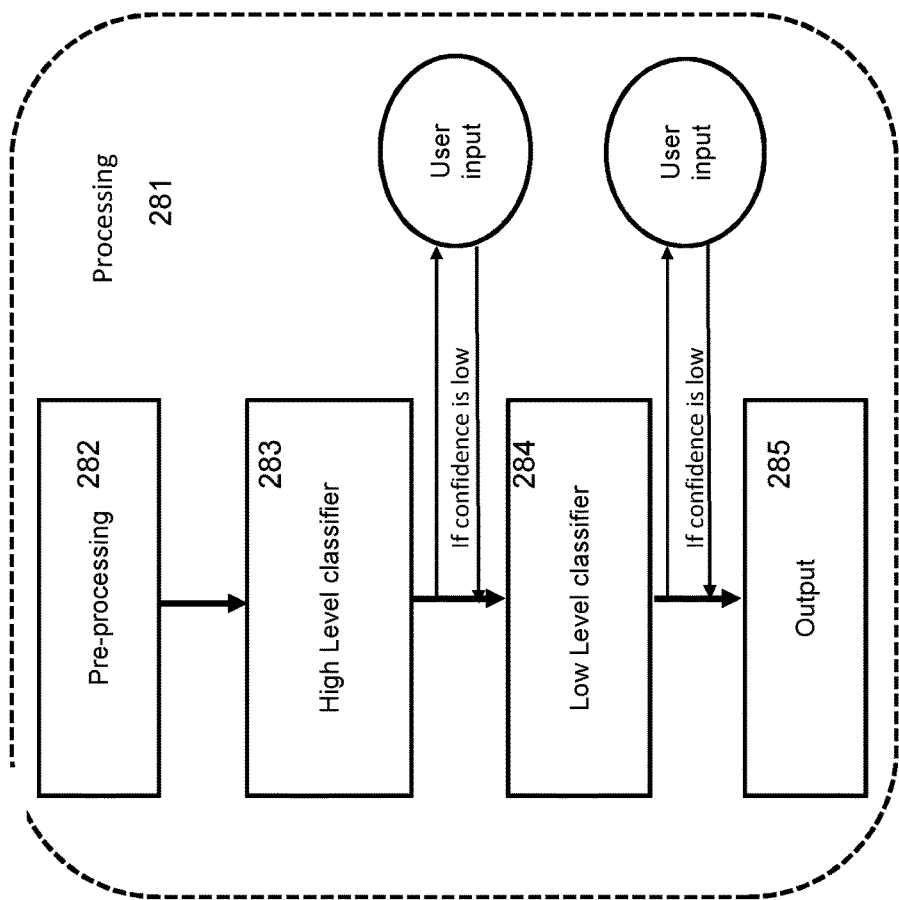
FIG. 12 shows the processing component of the AI engine.

A hierarchal set of Bi-LSTM algorithms forms the classification architecture of the processing module 280. Depending on number of categories answered, the classification system is divided. With reference to FIG. 12, the processing module 280 comprises a high-level classifier sub-module 283 and a low-level classifier sub-module 284. For example: if there are 100 categories, the high-level classifier module 283 performs a classification of 10 categories and the low-level classifier sub-module 284 categorizes specific 10 of each of the 10 categories. Alternatively, the high-level classifier module 283 categorizes 20 categories and low-level classifier sub-module 284 categorizes specific 5 of each of the 20 categories. This mainly depends on the architecture used and it will be appreciated that this configuration may change based on the performance. As previously mentioned, the AI module 280 is translatable therefore the specific division will be dependent on the application's domain.

Figure 11:
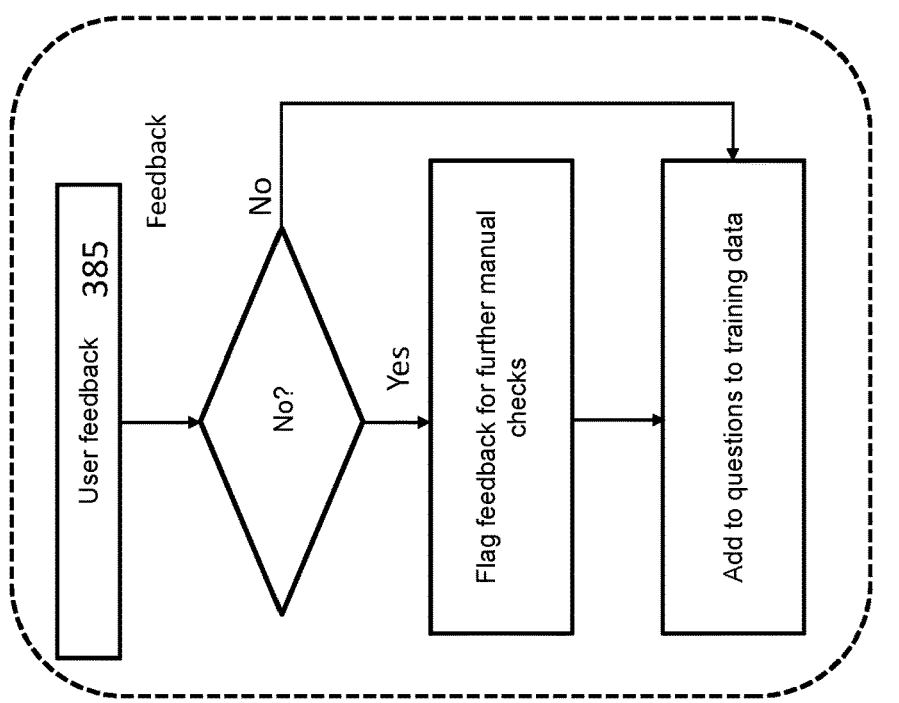
FIG. 11 shows the feedback processing and active learning component of the AI engine.

With reference to FIG. 11 and FIG. 12, the classification architecture produces output(s) 285. For each output 285 generated, a confidence value 286 is provided. A confidence value represents a probability of the output(s) 285 being associated with the input question. For example, a predetermined threshold for the confidence level to be met may be set by the system administrator (a manual input). The threshold may be decided based on the application, and this is usually set above 95%. If the threshold is met, then the answer(s) 285 are displayed as an output 380 to the user. If the threshold is not met, the user is provided with list of options to choose as to guide to fetch the correct answer.

Once the answer is displayed as output 380, the user is requested for a feedback 385. An exemplary process of providing user feedback is shown in FIG. 11. All user feedback may stored in the database 480 or other suitable databases.

To improve the performance of the system an active learning schema is implemented. An analysis is preferably carried out on the feedback data. For example, the feedback data is 'yes' in the case that the user is happy with the results obtained and 'no' otherwise. If the feedback data is 'yes' then the questions and answers are stored in a retraining database. The retraining database stores failure cases along with the response for review and model validation. If the feedback is 'no', then this is flagged for manual check and then added to the retraining database for algorithm retraining.

Applications and Interpretation

The foregoing examples and descriptions of embodiments of the present invention as described herewith may be implemented for example in GP triage rooms. However, the foregoing examples and descriptions of embodiments of the present invention have been presented only for purposes of illustration and description. They are not intended to be exhaustive or to limit the present invention to the forms disclosed. Accordingly, modifications and variations will be apparent to practitioners skilled in the art. In particular, it is envisaged that the search and machine learning principles may be applied to topics outside health care, such as sex education, product marketing and customer support and so on.

Further, the AI algorithms and avatars may be located on a client computing device. It will be understood however that not all of the logic for implementing the AI algorithms and/or avatar needs to be located on the client computing device and can be based on one or more server computer systems with a user interface being provided locally on the client computing device. Similarly, logic for implementing the avatar can be stored locally on the client computing device, while the information learned by the system (AI part) can be stored partially or entirely on one or more servers. The specific manner in which the AI algorithms and avatars are respectively hosted in not essential to the disclosure.

Those skilled in the art will further appreciate that aspects of the invention may be implemented in computing environments with many types of computer system configura-

The invention claimed is:

1. A method of producing an avatar video, the method comprising the steps of:
   providing a reference image of a person's face;
   using the reference image to provide a plurality of characteristic features representative of an initial facial model X0 of the person's face, wherein the plurality of characteristic features of the initial facial model XO comprise at least one set of landmarks and at least one latent descriptor representing an abstract appearance feature, the plurality of characteristic features defining facial position and facial pose dependent on a person speaking;
   providing a target phrase to be rendered over a predetermined time period during the avatar video and providing a plurality of time intervals t within the predetermined time period;
   generating, for each of said plurality of time intervals t, speech features from the target phrase, to provide a sequence of speech features, the speech features representing abstract quantifiers of audio and linguistic information; and
   using a recursive model comprising a sequence-to-sequence encoder decoder method to generate, from the initial facial model X0 and the sequence of speech features, a sequence of expected facial models for each of said plurality of time intervals t,
   wherein physical spatio-temporal dynamics of a facial model at each of said plurality of time intervals t are generated by solving a system of ordinary differential equations, ODEs, an expected facial position being derived from a recursive transformation of the speech features and the expected facial position of the facial model at a current time interval of said plurality of time intervals, which is sampled and being combined with the plurality of characteristic features of a facial model Xt at the current time interval to obtain the plurality of characteristic features of a next facial model Xt+1 in the sequence of expected facial models; and
   combining and decoding a sequence of facial models Xt with the initial facial model X0 to generate a sequence of face images to produce the avatar video.

2. A method according to claim 1, wherein the target phrase is provided as text data and/or audio data.

3. A method according to claim 1, wherein at least one of said speech features comprises a phonetic label.

4. A method according to claim 1, wherein the speech features are extracted with a phonetic classifier module using a Deep Convolutional Network (DCN).

5. A method according to claim 1, wherein the at least one latent descriptor is extracted using a Deep Convolutional Network (DCN).

6. A method according to claim 1, wherein the recursive model is generated with a Long Short-Term Memory network.

7. A method according to claim 1, wherein generating the sequence of face images comprises using a frame generator to synthesize frames from the sequence of facial models Xt.

8. A method according to claim 7, wherein the frame generator comprises a discriminator module using at least one loss function for reducing differences between the reference image and each of the facial models Xt in said sequence of facial models Xt.

9. A method of producing an avatar video, the method comprising the steps of:
   providing a reference image of a person's face;
   providing a plurality of characteristic features representative of a facial model X0 of the person's face, the plurality of characteristic features defining a facial pose dependent on a person speaking;
   providing a target phrase to be rendered over a predetermined time period during the avatar video and providing a plurality of time intervals t within the predetermined time period;
   generating, for each of said plurality of time intervals t, speech features from the target phrase, to provide a sequence of speech features; and
   generating, using the plurality of characteristic features and sequence of speech features, a sequence of facial models Xt for each of said plurality of time intervals t, wherein the sequence of facial models Xt is generated using a recursive model.

10. A method according to claim 9, wherein the speech features are extracted with a phonetic classifier module using a Deep Convolutional Network (DCN).

11. A method according to claim 9, wherein the plurality of characteristic features comprises at least one Active Shape Model landmark, and at least one latent descriptor representing abstract appearance features.

12. A method according to claim 11, wherein the at least one latent descriptor is extracted using a Deep Convolutional Network (DCN).

13. A method according to claim 9, wherein the recursive model comprises a sequence-to-sequence encoder decoder method.

14. A method according to claim 9, wherein the recursive model is generated with a Long Short-Term Memory network.

15. A method according to claim 9, wherein generating a sequence of face images comprises using a frame generator to combine the reference image with the sequence of facial models Xt.

16. A method according to claim 15, wherein the frame generator comprises a discriminator module using at least one loss function for reducing differences between the reference image and each facial models Xt in said sequence of facial models Xt.

17. A system for producing an avatar video, a method comprising the steps of:
   an image processing model for receiving a reference image of a person's face and for extracting a plurality of characteristic features representative of an initial facial model XO of the person's face, wherein the plurality of characteristic features of the initial facial model XO comprise at least one landmark and at least one latent descriptor representing an abstract appearance feature, the plurality of characteristic features defining facial position and facial pose dependent on the person speaking;
   a speech processing module for extracting a target phrase to be rendered over a predetermined time period during the avatar video and for providing a plurality of time intervals t within the predetermined time period;
   the speech processing module configured to generate, for each of said plurality of time intervals t, speech features from the target phrase, to provide a sequence of speech features, the speech features representing abstract quantifiers of audio and linguisic information; and
   an avatar rendering module configured to use a recursive model comprising a sequence-to-sequence encoder decoder method to generate, from the initial facial model XO and the sequence of speech features, a sequence of expected facial models for each of said plurality of time intervals t, wherein physical spatio-temporal dynamics of a facial model at each of said plurality of time intervals t are generated by solving a system of ordinary differential equations, ODEs, an expected facial position being derived from a recursive transformation of the speech features and the facial position of the facial model at a current time interval of said plurality of time intervals, which is sampled and being combined with the plurality of characteristic features of the facial model Xt at the current time interval to obtain the plurality of characteristic features of a next facial model Xt+1 in the sequence of expected facial models;

wherein the avatar rendering module comprises a frame generator configured to combine and decode a sequence of facial models Xt with the initial facial model X0 to generate a sequence of face images to produce the avatar video.

18. A system for producing an avatar video, a method comprising the steps of:
- an image processing model for receiving a reference image of a person's face and for extracting a plurality of characteristic features representative of a facial model XO of the person's face, the characteristic features defining a facial pose dependent on a person speaking;
- a speech processing module for extracting a target phrase to be rendered over a predetermined time period during the avatar video and for providing a plurality of time intervals t within the predetermined time period;
- the speech processing module configured to generate, for each of said plurality of time intervals t, speech features from the target phrase, to provide a sequence of speech features; and
- an avatar rendering module for generating, using the plurality of characteristic features and sequence of speech features, a sequence of facial models Xt for each of said time intervals t, wherein the sequence of facial models Xt is generated using a recursive model.

19. An interactive system for providing an answer to a user, the system comprising:
- a database comprising an indexed question library and a plurality of responses, wherein the plurality of responses comprise at least one avatar video produced using a system according to claim 18;
- a processing module for providing a correlation between the indexed question library and the plurality of responses;
- input means for receiving a question from the user as user input;
- wherein the processing module is configured to search keyword information in the indexed question library based on the user input; and
- providing at least one response to the user based on said correlation.

20. A healthcare information system comprising an interactive system according to claim 19.

* * * * *

UNITED STATES PATENT AND TRADEMARK OFFICE
CERTIFICATE OF CORRECTION

| | |
|---|---|
| PATENT NO. | : 11,900,518 B2 |
| APPLICATION NO. | : 17/441791 |
| DATED | : February 13, 2024 |
| INVENTOR(S) | : Peter Alistair Brady et al. |

It is certified that error appears in the above-identified patent and that said Letters Patent is hereby corrected as shown below:

On the Title Page

In item (73) Assignee:
"VirtTari Limited"
Should be changed to:
--VirtTuri Limited--

Signed and Sealed this
Twenty-third Day of April, 2024

Katherine Kelly Vidal
*Director of the United States Patent and Trademark Office*